(12) United States Patent
Kleyman et al.

(10) Patent No.: US 10,004,552 B1
(45) Date of Patent: Jun. 26, 2018

(54) END EFFECTOR STRUCTURE FOR STAPLING APPARATUS

(71) Applicants: Gennady I Kleyman, Brooklyn, NY (US); Annaniy Berensteyn, Edgewater, NJ (US)

(72) Inventors: Gennady I Kleyman, Brooklyn, NY (US); Annaniy Berensteyn, Edgewater, NJ (US)

(73) Assignee: EXPANDOHEAT, L.L.C., Atlantic Heights, NJ (US)

( * ) Notice: Subject to any disclaimer, the term of this patent is extended or adjusted under 35 U.S.C. 154(b) by 384 days.

(21) Appl. No.: 14/819,731

(22) Filed: Aug. 6, 2015

Related U.S. Application Data

(60) Provisional application No. 62/135,362, filed on Mar. 19, 2015.

(51) Int. Cl.
| | |
|---|---|
| *A61B 18/18* | (2006.01) |
| *A61B 18/08* | (2006.01) |
| *A61B 18/10* | (2006.01) |
| *A61B 17/072* | (2006.01) |

(52) U.S. Cl.
CPC .......... *A61B 18/085* (2013.01); *A61B 17/072* (2013.01); *A61B 18/10* (2013.01); *A61B 18/1815* (2013.01); *A61B 2017/07257* (2013.01); *A61B 2018/183* (2013.01)

(58) Field of Classification Search
CPC . A61B 18/085; A61B 18/1815; A61B 17/072; A61B 2018/183; A61B 2017/027257
See application file for complete search history.

(56) References Cited

U.S. PATENT DOCUMENTS

| | | | | |
|---|---|---|---|---|
| 2002/0091427 A1* | 7/2002 | Rappaport | ......... | A61B 18/1492 607/101 |
| 2003/0125720 A1* | 7/2003 | Woodard | ........... | A61B 18/1492 606/15 |
| 2005/0203504 A1* | 9/2005 | Wham | ............... | A61B 18/1442 606/34 |
| 2007/0102472 A1* | 5/2007 | Shelton, IV | ..... | A61B 17/07207 227/175.1 |
| 2008/0125765 A1* | 5/2008 | Berenshteyn | .......... | A61B 18/18 606/33 |
| 2009/0182398 A1* | 7/2009 | Kleyman | ............... | A61B 18/18 607/98 |
| 2009/0204112 A1* | 8/2009 | Kleyman | ............... | A61B 18/18 606/33 |

* cited by examiner

*Primary Examiner* — Daniel Fowler

(57) ABSTRACT

An end effector structure (e.g. jaws structure or similar), configured with an internal antenna for delivery of electromagnetic energy in microwave range to a straight, curved or circular end effector structure in which the portion of end effector structure includes a microwave absorbing material that absorbs microwave energy emitted by the antenna and transfers microwave energy into the heat. Such end-effector also includes surgical fasteners or staples for strengthening tissue, providing a hemostasis, tissue joint and/or welding. The microwave antenna is connected by a coaxial cable with a microwave generator. The heat generated in the microwave absorbing material is applied to the treated material (e.g. tissue) by means of capturing material in the end effector (jaw structure) and heating the tissue to the desired temperature either before, during or after a stapling procedure.

20 Claims, 6 Drawing Sheets

END EFFECTOR STRUCTURE FOR STAPLING APPARATUS

Priority on Provisional Patent Application 62/135,362 filed 19 Mar. 2015 is claimed and is incorporated herein by reference.

FIELD OF THE INVENTION

The present invention is related to surgical staplers and more particularly to end effector structure of a stapling apparatus for applying a plurality of surgical fasteners or staples to the body tissue with ability to heat the tissue retained and compressed between the end effector to a desired temperature.

BACKGROUND OF THE INVENTION

In various open, endoscopic, and/or laparoscopic surgeries it may be necessary to coagulate, seal, and/or fuse tissue, even before applying a plurality of surgical fasteners or staples to the body tissue, to insure reliable seal. To do that, the tissue is captured within an end effector of a surgical instrument in order to cause thermal effects within the tissue. The thermogenic energy also strengthens tissue in proximity to a staple line and knife cut line and provides hemostasis along the staple and cut lines formed by the staples and a knife blade during surgical stapling. The use of thermogenic energy provides short-term hemostasis and sealing, and reduces or prevents the staple line and the cut line bleeding, while the stapling features provide short and long-term tissue strength and hemostasis.

In general, the delivery of heat energy to the captured tissue elevates the temperature of the tissue and, as a result, the energy can at least partially denature proteins within the tissue. The proteins, such as collagen, for example, may be denatured into a proteinaceous amalgam that intermixes and fuses, or "welds", together as the proteins renature.

It would be desirable to have an end effector structure of stapling devices combining the structural and functional aspects of stapling instruments and heat tissue compressed between jaws of end effector to desired temperature to improved hemostasis by using thermogenic energy to cause coagulation or cauterization and surgical fasteners to staple the tissue, either before, during or after the use of thermogenic energy.

Prior usage of RF energy to provide tissue hemostasis prior to surgical stapling was not reliable, because tissue heating by RF energy depends of tissue parameters (e.g. wet versus dry), and often during RF heating, tissue charring and smoke generation will occur and because of tissue sticking to the RF electrodes, with a chance that treated area will be disrupted and bleeding can occur.

Usage of known resistive heating technology in surgical staplers very problematic because of significant thermal inertia of this type of heaters, which leads to a long heating and cooling time. Further problems arise from the resistance heater heating up the tissue only by conventional heat exchange, which can be very long process because of tissue low heat conductivity, which will lead to long heating time, especially for thick tissue, which may also influence penetration and uniformity of heating throughout the tissue.

SUMMARY

An embodiment of the present invention provides an end effector structure (e.g. jaws structure or similar), configured with an internal antenna for delivery of electromagnetic energy in microwave range to an end effector structure in which the portion of end effector structure includes a microwave absorbing material that absorbs microwave energy emitted by the antenna and transfers microwave energy into the heat. Such end-effector also includes surgical fasteners or staples for strengthening tissue, providing a hemostasis, tissue joint and/or welding. The microwave antenna is connected by a coaxial cable with a microwave generator. The heat generated in the microwave absorbing material is applied to the treated tissue by means of capturing tissue in the end effector (jaw structure) and heating the tissue to the desired temperature either before, during or after a stapling procedure. Staplers can be straight, curved or circular.

One embodiment of the apparatus is a surgical stapler end-effector that includes a first body portion defining a surface against which a plurality of surgical staples are driven when ejected from a second body portion and the second body portion houses the plurality of surgical staples and at least one of those body portions includes a portion made from a microwave absorbing material and a microwave antenna to emit microwave energy.

Another embodiment of the apparatus includes a first body portion that includes an anvil plate, which has a surface that includes a plurality of staple-receiving recesses, which define a fastener forming surface, are made from microwave absorbing material and inside of this portion located a microwave antenna to emit microwave energy and this anvil plate also includes a blade slot for passing the blade to create a cut line. The anvil plate or a portion of anvil plate can be made from microwave absorbing material. When the microwave antenna emits microwave energy, the microwave absorbing material converts this energy (completely or partially) into heat energy and this heat energy heats up the tissue compressed by the end effector. Furthermore, to control the tissue temperature this end effector portion can include a temperature control element (thermocouple, thermistor, fiber optic temperature control element, etc.) to provide a corresponding signal to a microwave generator controllable in response to a signal from the temperature control element. Alternatively, the temperature can be controlled by visual observation.

Another embodiment of the apparatus includes a second body portion or housing plate that houses the plurality of surgical staples, and all or part of this housing plate is made from microwave absorbing material. The second body portion typically includes a microwave antenna, a blade slot for passing the blade to create a cut line. When the microwave antenna emits microwave energy, the microwave absorbing material converts this energy (completely or partially) into heat energy and this heat energy heats up the tissue compressed by the end effector. Additionally, it also can heat up a plurality of surgical staples (staples can be made from metal or non-metal materials) retained in the second body portion.

Therefore, the invention by its various embodiments, provides a stapling and heating apparatus which uses thermogenic energy and staples for providing hemostasis, tissue joining and/or welding, and also strengthens tissue in proximity to a staple line and provides hemostasis along the staple line ("staple line" being a common term seen on the tissue only after the stapler was fired, where on the drawings, the staples are inside the pockets) to reduce or prevent staple line and cutting line bleeding and increase a seal quality and strength.

Thus, one embodiment of the present invention comprises a surgical apparatus, comprising:

a first elongated member having a first surface and a first dimension along which a plurality of staples are disposed and movable through said first surface, at least a portion of said first elongated member comprising a microwave absorbing material providing heat output from said first surface in response to absorbed microwave energy and further including a microwave antenna disposed to radiate microwave energy into said microwave energy absorbing material;

a second elongated member having a second surface substantially confronting said first surface including a staple anvil disposed to confront said plurality of staples when said first surface is disposed to confront said second surface, said second elongated member being movable relative said first elongated member, at least a portion of said second elongated member including a microwave absorbing material providing heat output from said second surface in response to absorbed microwave energy and further including a microwave antenna disposed to radiate microwave energy into said microwave energy absorbing material; and a connecting member retaining said first elongated member and said second elongated member and having a member selectively movable to urge said first surface and said second surface toward each other and apart from each other.

A further embodiment of the present invention comprises a method of treating material proximal an incision, comprising:

engaging opposing surfaces of a target material between microwave absorbing structures;

providing heat from said microwave absorbing structures to said target material controlling said microwave energy according to target material characteristics heating said target material sufficient to provide at least one of material hemostasis, tissue joining, welding, and strengthening in proximity to a target material region; and dividing said target material in said target material region.

BRIEF DESCRIPTION OF THE DRAWING

These and further features of the present invention will become more readily apparent to those skilled in the art from the following detailed description of the apparatus taken in conjunction with the drawing figures, wherein.

DETAILED DESCRIPTION

Figure 1:
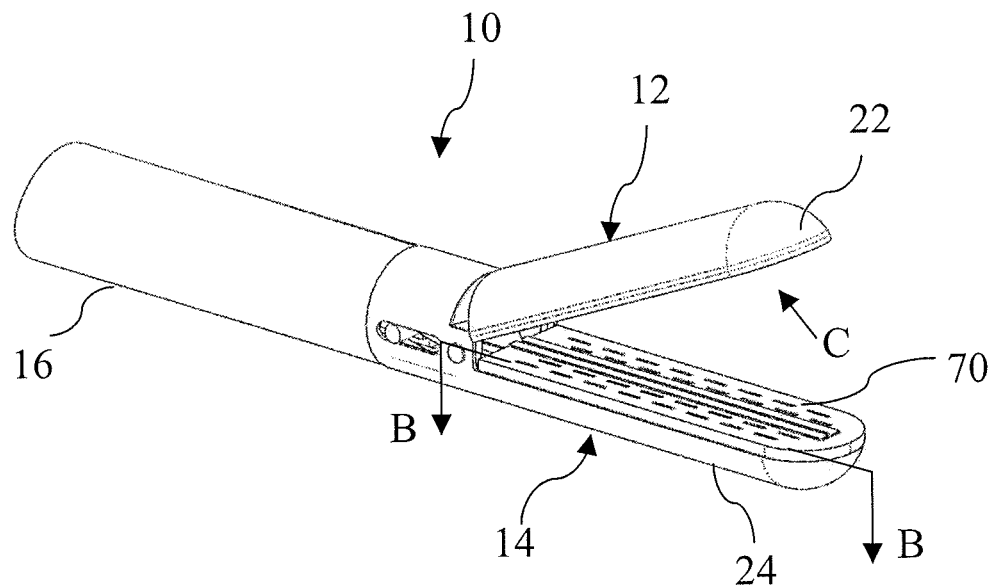
FIG. 1 is a perspective view of end effector structure for stapling apparatus.
Figure 2:
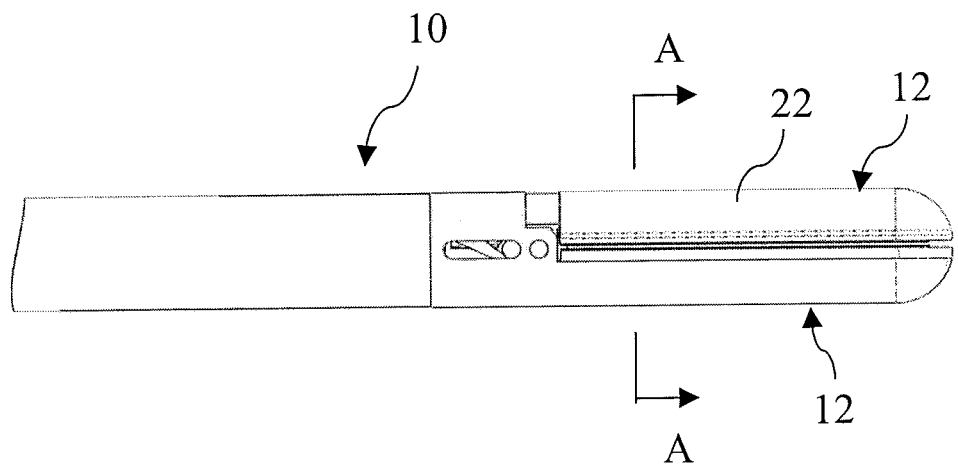
FIG. 2 is a side view of the apparatus of FIG. 1 in closed state.

Reference will now be made in detail to several views of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity, directional terms, such as rear and front may be used with respect to the drawings. These and similar directional terms should not be construed to limit the scope of the invention in any manner. The term "microwave frequency range" refers herein to frequencies between 30 MHz and 30,000 MHz inclusive, where MHz is one million Hertz, and the term "radio-frequency range" refers herein to frequencies between 30 kHz and 30 MHz, where kHz is one thousand Hertz. Although the following description operates via a microwave energy emitter, the present invention is operable by various electromagnetic energy sources and is not limited to microwave energy.

The energy absorbing part of the jaw structure is preferably made from microwave absorbing material by means of extrusion, injection molding or machining. The microwave absorbing material can be silicone impregnated with silver (Ag) and glass fillers, which are generally unaffected by exposure to temperatures reaching 500° F. Glass fillers can be regular glass in form of small beads and other fillers include nickel (Ni), copper (Cu), Aluminum (Al), which can each be used as a single filler or combined with other materials, for example combinations of Ag/Cu; Ag/Al; Ag/Ni; Ag/Glass and others. Silicone is a preferred material due to compatibility to the human body, and other materials that can be used include fluorosilicone, fluorocarbon, thermoplastic rubber and ethylene propylene diene monomer, and can be thermoplastic materials, such as rigid urethane impregnated with polyamide and thermoplastic urethane impregnated with carbonyl iron powder, iron silicide and ferrites fillers are utilized, and can be ceramic with different fillers, in view of advantageous microwave absorbing properties. The external portion of the structure is preferably made from a metal. The microwave antenna surrounded by microwave absorbing material and when antenna emit microwave energy and microwave absorbing material transfers this energy into the heat and heat the treated tissue either before, during or after the stapling is executed.

The end effector (jaw structure) is further preferably equipped with temperature sensors connected to control the amount of heat generated in the energy-absorbing portion of the jaw structure, which transfers the heat to treated tissue, thus insuring the proper heating of the tissue.

DESCRIPTION OF THE REFERENCE ELEMENTS

10—is a stapling apparatus end effector embodiment
12—is a upper (anvil) structure
14—is a lower (staples) structure
16—is a cannula portion of stapling apparatus connected to a stapler handle (not shown)
22—is a metal jaw body of anvil portion of the end effector
24—is a metal jaw body of staple portion of the end effector
26—is a support in staples portion
28—staples pocket body, made from microwave absorbing material
30—is a microwave antenna located in staple portion
32—is an anvil staples forming portion, made from microwave absorbing material
36—is a microwave antenna located in anvil portion
40—staples
42—is a drivers to push staples against anvil pockets
42—staples drivers 44—is a staple forming pockets in anvil portion of the end effector
48—track for staples drivers
50—cutting blade
52—is a blade channel in staple portion of end effector
54—is a blade channel in anvil portion of end effector
56—staples lifting wedge
58—blade link
60—is an anvil staples forming portion
62—metal shield (foil) for insert in anvil portion
64—is an insert in anvil portion, made from microwave absorbing material
70—staples pocket body
72—metal shield for insert in staple portion
78—is an insert in staples portion of end effector
80—anvil movement bracket
82—is an anvil portion pivotal pins
84—is a hinge hole for pins 82
86—is a travel grove in staples portion
88—is an engagement pins for travel in anvil portion grove 90
90—anvil portion pin grove
92—pins 88 connecting link
96—link for pins 88 movement
100—is a stapler apparatus end effector second embodiment
102, 104—is a temperature sensors located in anvil and staples portions
106—temperature sensor connecting wire
114—is a coaxial cable which supplying microwave energy to microwave antenna located in anvil portion
112—is a coaxial cable to supply microwave energy to antenna located in staple portion.
120—target material (tissue)

As shown in the figures, stapling apparatus end effector structure 10 comprises an anvil (upper) jaw structure 12 and a staples (lower) jaw structure 14. The anvil structure 12 includes a staple forming plate 60 having a substantially planar surface, and including staples forming pockets 44.

Figure 4:
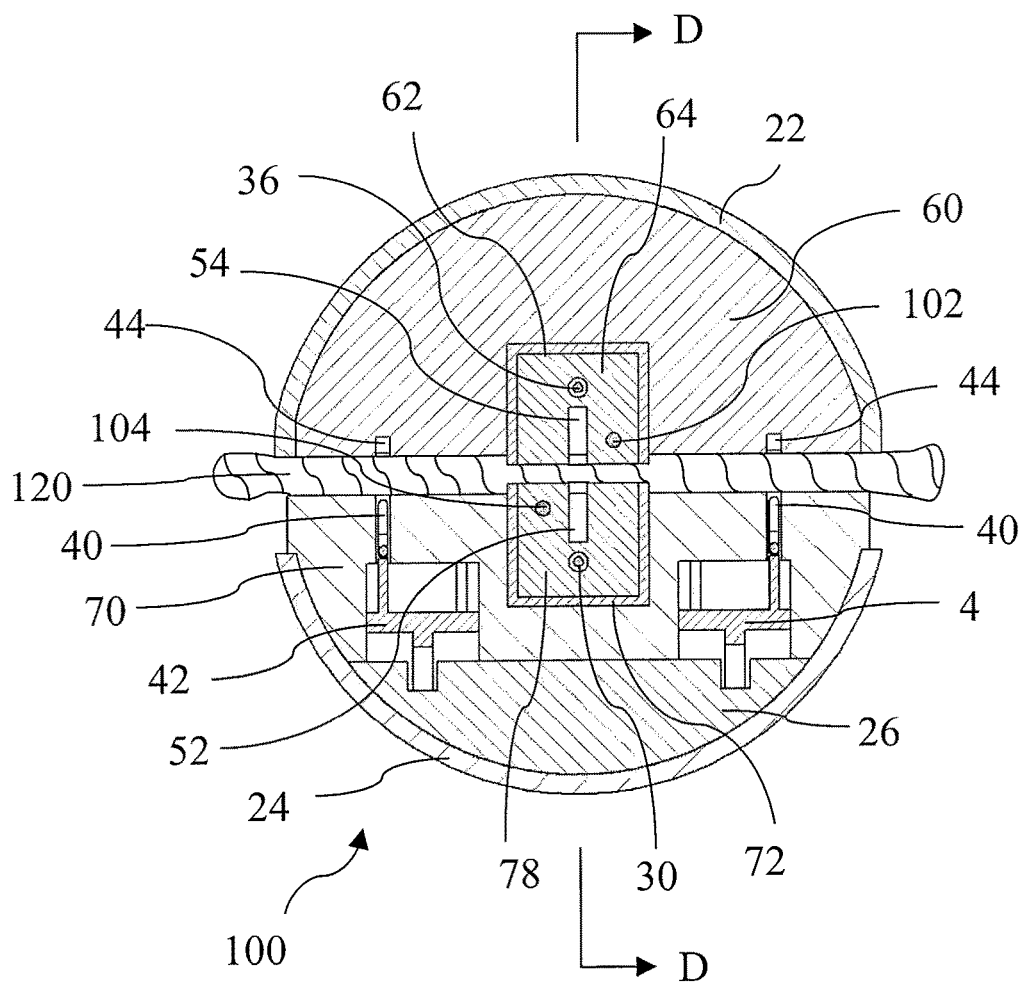
FIG. 4 is a cross-sectional view of the apparatus of FIG. 1 taken along line A-A on FIG. 2 with another embodiment.
Figure 5:
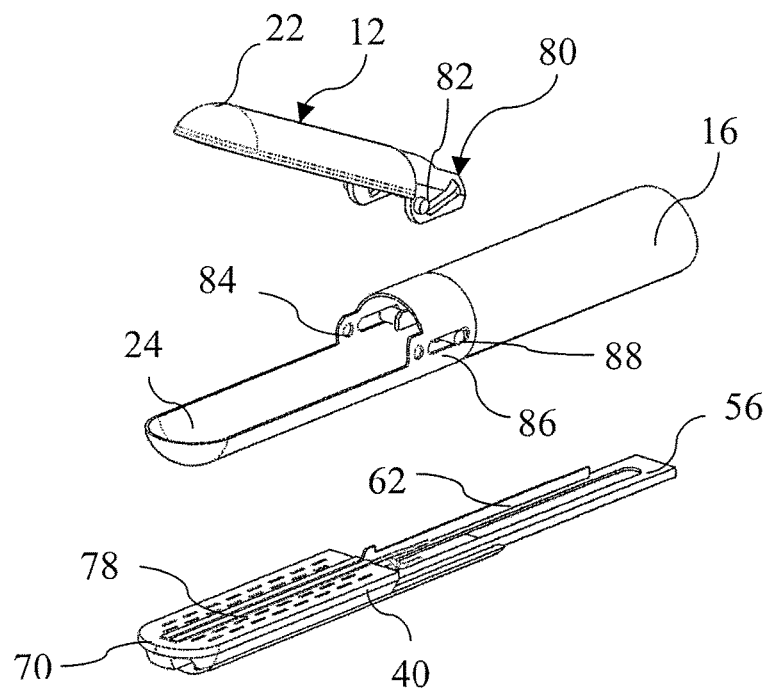
FIG. 5 is a partial exploded view of the end-effector structure for a stapling apparatus.
Figure 6:
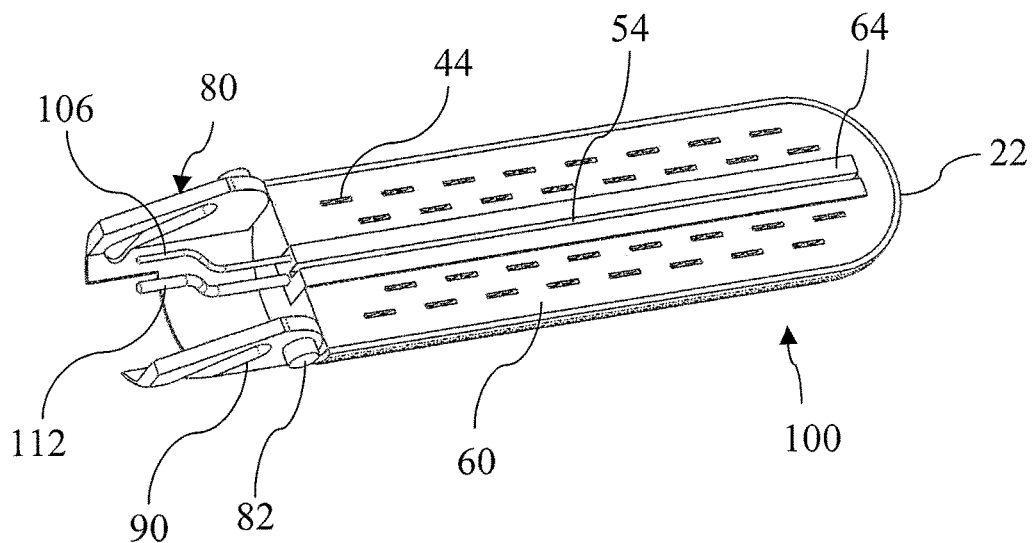
FIG. 6 is a directional view C from FIG. 1 that shows the upper (anvil) portion of stapling apparatus.
Figure 7:
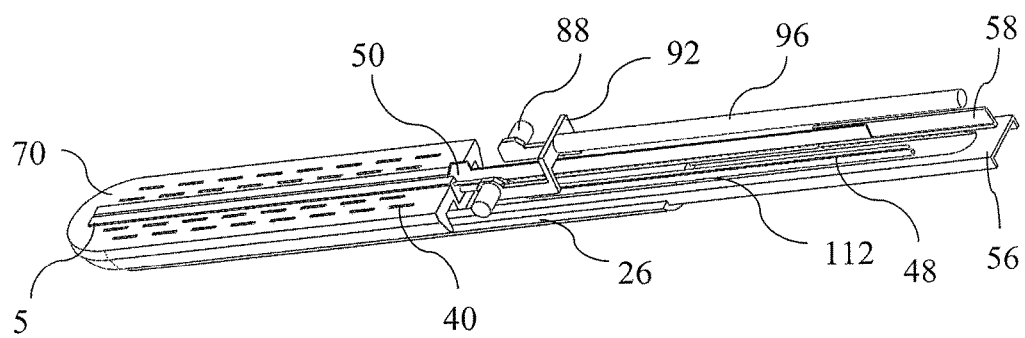
FIG. 7 is a perspective view of the staples portion of an embodiment of a stapling apparatus.
Figure 8:
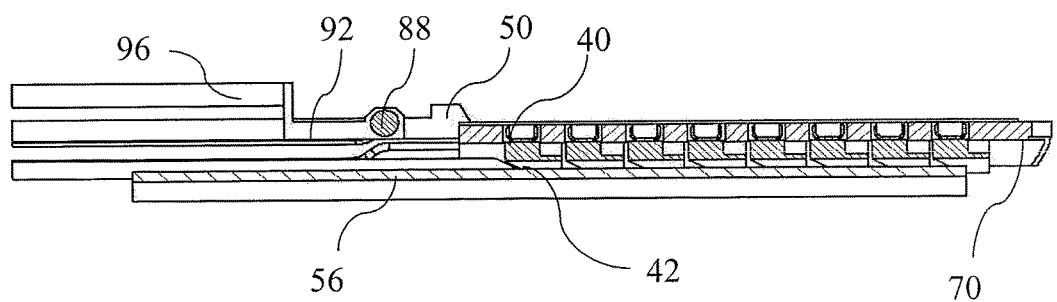
FIG. 8 is a cross section of a side view of an embodiment of a lower (stapling) structure.

In an alternate embodiment 100, of FIGS. 4, 6, the anvil structure 12 also includes an insert 64 made from microwave energy absorbing material and a microwave antenna 18 located inside the insert 64 which is connected with coaxial cable 112 to a microwave signal generator (not shown) to provide energy to the antenna 36. Additionally this insert 64 extends along the length of the end-effector lower jaw 12 and includes a blade channel 54 to guide the travel of a cutting blade (e.g. 50) along the channel 54 length, and within this insert 64 an optional temperature sensor 102 can be located. A metal (or other microwave reflective material) shield 62 may be disposed between the insert 64 and anvil forming plate 60.

Figure 3:
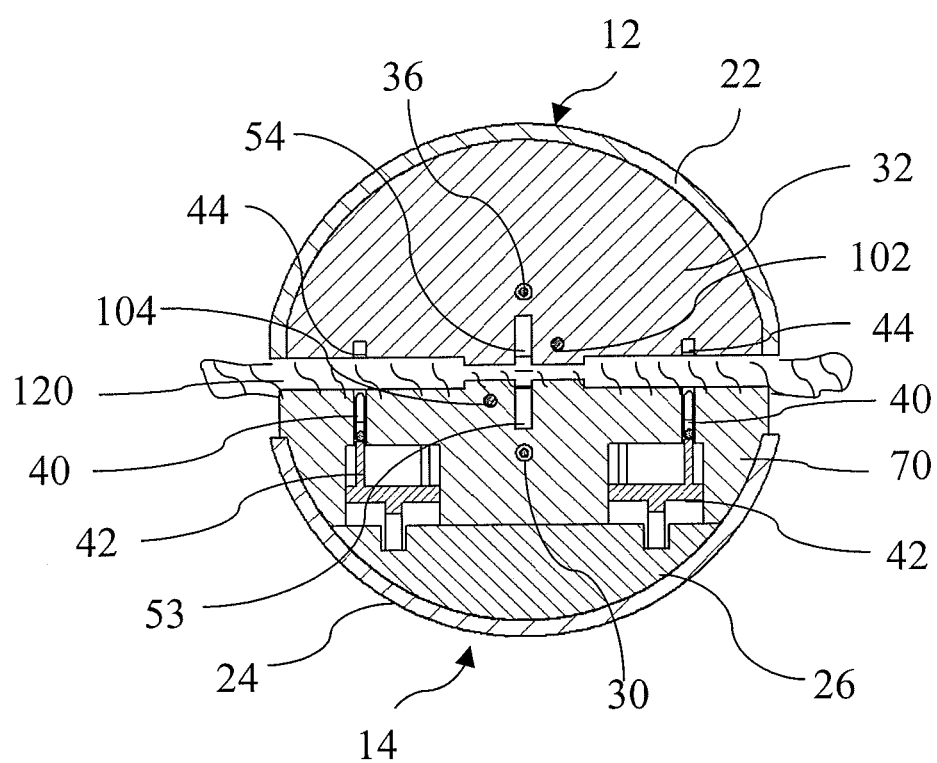
FIG. 3 is a cross-sectional view of the apparatus of FIG. 1 taken along line A-A on FIG. 2.

Structurally, the various embodiments may provide the anvil portion elements are incorporated with an anvil metal body 22. Alternatively, e.g. in the embodiment of FIG. 3, the staples forming plate 32 (or 60) can be made from microwave absorbing material and microwave antenna 36 can be located inside this portion, and it can be proximal the anvil surface facing the opposing jaw 14, and it can be proximal the channel 54.

The staples structure 14 includes a staples holding body 70 and staples 40 located in staples holding body 70 individual recesses or 'pockets', typically one staple to a pocket. In one embodiment 100, the staples structure 14 may also include an insert 78 made from microwave absorbing material (similar to that describe above with respect to the anvil 12 insert 64) and inside this insert 78 is located a microwave antenna 30, which is connected to a coaxial cable 114 similar to cable 112, which supplies microwave energy to the microwave antenna 30 from a microwave generator (not shown), which antenna radiates microwave energy to heat insert 78 microwave absorbing material, and the staples structure 14 also can include a temperature sensor 104 and may further include a metal (or other microwave reflector) shield between insert 78 and staples pocket body 70. Additionally, the staples structure 14 includes a blade channel 52 to guide the movement of the cutting blade 50 along the length of the structure 14 and staple drivers 42 for pushing staples 40 towards the anvil pockets 44 through the substantially planar (anvil 12) facing surface including pockets in material for staples formation and are typically incorporated within the staple portion metal body 24. Alternatively in the various embodiments of the present invention, the staples holding body 70 can be made from microwave absorbing material and microwave antenna 30 can be located inside this portion (e.g. FIG. 3) to generate heat therein which radiates through the surface to the target material or tissue. Antennas 30, 36 may be substantially within the microwave energy absorbing materials, or proximal the respective structure (12, 14) surfaces and/or proximal the blade channels 52, 54.

Figure 9:
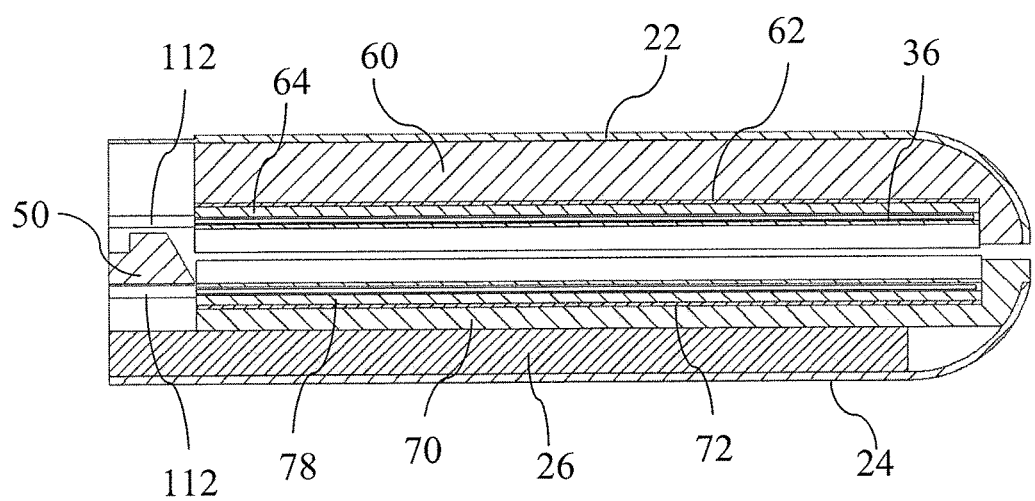
FIG. 9 is a longitudinal cross-sectional view taken along line D-D on FIG. 4

The upper (anvil) structure 12 and the lower (staples) structure 14 are connected by a hinge-like structure formed from an anvil movement bracket 80 radially extending pivot pin 82 engaging a hinge hole 84 in a portion of the lower structure 14, e.g. the jaw body 24, permitting the upper (anvil) structure 12 and lower (staples) structure 14 to pivot apart distal from the hinge formed by pivot pin 82 and hole 84. Furthermore, in the exemplary embodiments, the pivot opening is controlled by axial motion of a mechanical link control 96 which is connected to a axially movable link member 92 which include radially extending pins 88 which engage anvil movement bracket 80 pin grooves or slots 86 and 90. The pins 88 grooves 90 extend along a plane at an angle to the direction the lower (staples) structure 14 surface extends, such that when the pins move substantially axially (e.g. at an angle to the groove plane), the pins 88 urge the grooves or slots 90 to also be disposed on the direction of the pin 88 motion and slots 86, causing the upper (anvil) structure 12 and lower (staples) structure 14 (distal from the pivot pin 82) to pivot open to separate and receive the target tissue therebetween. Thereafter, withdrawal of the pins 88 (reverse motion) urges the upper (anvil) structure 12 and the lower (staples) structure 14 to close (e.g. as shown in FIG. 9) and compress the target tissue or material 120, between the facing surfaces of the anvil 12 and staples 14 structures, permitting the process described herein to be carried out. In one embodiment, a region of the anvil 12 and staples 14 structures, proximal the blade channels 52, 54, may be raised slightly from the respective surfaces of the anvil 12 and the staples 14 structures to form facing plateaus.

The staples lifting wedge 56 is similarly axially moved into the region of the staples 40 and engage the staple drivers 42 by an inclined leading edge to urge the staple drivers and corresponding staples 40 through the structure 14 surface and through the tissue (not shown) and against the anvil structure 14 typically along a line proximal the anticipated incision.

When typically in use, the stapler end effector structures compress the tissue (e.g. between the upper (anvil) structure 12 and the lower (staples) structure 14) before stapling, the microwave energy can be supplied thru the coaxial cables (such as 112) to the corresponding microwave antennas 36 and 30 located in the anvil and the staples portions respectively of the end effector. Similarly in the alternate embodiment 100, when the microwaves antennas 30, 36 emit microwave energy into inserts 62, 78, the anvil and the staples inserts 62 and 78 transfers microwave energy into heat energy and heat up the compressed tissue to the desire temperature, while the (optional) corresponding sensors 102 and 104 (e.g. temperature or other characteristic) provide a signal to the microwave signal generator (not shown) control the tissue heating. The drivers 42 then push the staples 40 against the anvil pockets 44 and seal the compressed tissue. After the cutting blade 50 cuts the tissue while moving thru the knife channels 52 and 54 along the length of the anvil 12 and staples 14 structures. Microwave energy can by supplied either before, during or after a stapling process and this sequence can be determined by the tissue type or procedure.

Further embodiments of present invention include modifications determined by the particle density of the microwave absorbing material and a ratio or proportion of microwave energy absorbed by this material and converted into heat energy and microwave energy can be selectively changed. Some or all of the unconverted microwave energy passes to the effector tissue (or material between the anvil 12 and staples 14 structures) to be absorbed there at the surface or more deeply below the surface. Therefore during tissue heating by present invention compressed by end effector tissue will be treated by conventional heating by contacted surfaces of end effector (this heat will provide hemostasis to upper level of tissue) according to the present invention and microwave heating by transmitted microwave energy which will heat up deeper layers of tissue and combination of this heating will dramatically shorten heating tissue time. Additionally, there are different types of tissue e.g. epithelial, connective, nervous, and muscle each with different physical properties (water content, for example) and therefore with different response to microwave energy. Also, the thickness of treated tissue may vary for different procedures. By changing the ratio between the amount of heat produced by absorption of microwave energy (heat conduction) and the amount heat produced by transmission of microwave energy to tissue (direct heating of tissue by microwave energy) the most effective ablation (e.g. complete or substantially complete ablation in the treated region) of tissue can be achieved (avoiding overheating, charring, etc.) for a particular procedure. According to the present invention, optimal ablation may be achieved.

For example, for thin tissue up to 3 mm thick the relationship between the density of particles in a microwave absorbing material and particles type (silver, carbon, etc.) can be selected to transfer 90% to 100% of microwave energy will transferred by heat conduction (absorbed microwave energy) and 10% to 0% will be transmitted microwave energy. For thicker tissue from 3 mm up to 7 mm tissue, microwave absorbing material will be selected to transfer 60% to 90% microwave energy by heat conduction (absorbed microwave energy) and the rest of it will be transmitted microwave energy. For tissue 7 mm and up microwave absorbing material can be selected to transfer 20% to 60% of microwave energy by heat conduction (absorbed microwave energy) and 40% to 60% it will be transmitted microwave energy. The ratio between the amount of heat produced by absorption of microwave energy (heat conduction) and the amount heat produced by transmitted of microwave energy to tissue (direct heating of tissue by microwave energy) is not limited to the thickness of the tissue and can also be customize for specific tissue types.

The U.S. Pat. Nos. 8,521,302 and 8,343,114 are incorporated herein by reference. Embodiments of present invention include various fabrication (e.g. by molding, machining, etc.) of anvil and staples portion of stapler and various subcomponents thereof from microwave absorbing material. Moreover in addition to extending along a straight dimension or axis, according to the present invention as taught herein, the end-effector anvil and staples structures can extend along a curved or an annular path length having the corresponding modifications to the related and contained components. Also within the scope of the present invention is a surgical instrument as described above, but with microwave absorbing material disposed within a single elongated member and a surgical instrument as described above but with an antenna disposed within a single elongated member. Further modifications and substitutions by one of ordinary skill in the art are within the scope of the present invention which is not to be limited except by the claims which follow.

What is claimed is:

1. A surgical apparatus, comprising:
a first elongated member having a first surface and a first dimension along which a plurality of staples are disposed and movable through said first surface, at least a portion of said first elongated member comprising a microwave absorbing material providing heat output from said first surface in response to absorbed microwave energy and further including a microwave antenna disposed to radiate microwave energy into said microwave energy absorbing material;
a second elongated member having a second surface substantially confronting said first surface including a staple anvil disposed to confront said plurality of staples when said first surface is disposed to confront said second surface, said second elongated member being movable relative said first elongated member, at least a portion of said second elongated member including a microwave absorbing material providing heat output from said second surface in response to absorbed microwave energy and further including a microwave antenna disposed to radiate microwave energy into said microwave energy absorbing material; and
a connecting member retaining said first elongated member and said second elongated member and having a member selectively movable to urge said first surface and said second surface toward each other and apart from each other, wherein
at least one of said first elongated member microwave antenna and said second elongated member microwave antenna is disposed to also radiate microwave energy, unconverted to heat output, toward the corresponding opposing said second surface and said first surface.

2. The surgical apparatus of claim 1, wherein at least one of said first elongated member microwave antenna and said second elongated member microwave antenna is disposed proximal said corresponding first surface and said second surface.

3. The surgical apparatus of claim 1, wherein said first elongated member includes an elongated dimension, and includes recess disposed along said elongated dimension.

4. The surgical apparatus of claim 3, wherein said recess retains a knife therein.

5. The surgical apparatus of claim 3, wherein said first elongated member microwave antenna is disposed proximal to said recess.

6. The surgical apparatus of claim 1 wherein at least one of said first surface and said second surface includes a plateau region.

7. The surgical apparatus of claim 1, wherein said first elongate member further includes a staple driver disposed to selectively move said staples through said first surface.

8. The surgical apparatus of claim 7, wherein said first elongated member includes a staple driver thereon.

9. The surgical apparatus of claim 1, wherein said microwave absorbing material comprises at least one of silicone, elastomers and ceramics, impregnated with at least one of silver (Ag), nickel (Ni), copper (Cu), Aluminum (Al) and glass fillers.

10. The surgical apparatus of claim 1, said second elongated member further including a connecting member control linkage having a slot angled relative to said second surface longitudinally extending dimension and further including movable pins received in said angled slot causing said first elongated member to move relative to said first elongated member.

11. The surgical apparatus of claim 1, at least one of said first elongated member and said second elongated member includes a microwave energy absorbing insert.

12. The surgical apparatus of claim 11, further including a metal shield surrounding said insert.

13. The surgical apparatus of claim 1, further including heat output temperature monitor.

14. Method of treating material, comprising:
providing opposing structures wherein at least one of said opposing structures includes a microwave energy absorbing material;
engaging at least one surface of a target material with said microwave energy absorbing material;
heating said microwave energy absorbing material with microwave energy; and
providing heat to said target material partially from said heated microwave absorbing material and partially from at least a portion of said radiated microwave energy.

15. The Method of claim 14, wherein said region further includes stapling said target material along a staple line, and at least one of hemostasis, target material joining, target material welding, and strengthening said target material in proximity to said staple line.

16. The Method of claim 14, further including monitoring the temperature of said heat provided and adjusting said microwave energy in response thereto.

17. The Method of claim 14, further including dividing said target material along a line.

18. The Method of claim 14, further including determining target material characteristics and providing microwave energy to said microwave absorbing material according to said target material characteristics.

19. The method of claim 14, further including transmitting microwave energy directly to said target material wherein a ratio of said heat applied to said target material and target material received microwave energy ablates said target material.

20. A surgical instrument for treating a biological tissue, comprising;
a first elongated member;
a second elongated member mounted and movable relative said first elongated member having an open and a closed position of respectively greater and lesser distance between said first and elongated member and said second elongated member, wherein at least one of said first elongated member and said second elongated member includes microwave absorbing material, and said first elongated member and said second elongated member in said closed position include a region therebetween capable of receiving tissue therein; and
at least one microwave antenna disposed to radiate microwave energy into said microwave absorbing material and into a region of said closed position between said first elongated member and said second elongated member, wherein
at least one antenna is operative to radiate a microwave energy in said closed position so that the radiated electromagnetic energy is partially absorbed by said microwave absorbing material having a selected amount of microwave energy absorption, and partially directly transmitted into said region having a ratio of heat produced by said microwave absorbing material and an amount of heat produced by transmission of microwave energy into said region is controlled to ablate tissue disposed within said region according to a tissue type and a tissue thickness.

* * * * *